(12) United States Patent
Schipper et al.

(10) Patent No.: US 11,432,898 B2
(45) Date of Patent: Sep. 6, 2022

(54) TRACING PLATFORMS AND INTRA-OPERATIVE SYSTEMS AND METHODS USING SAME

(71) Applicant: INTELLIJOINT SURGICAL INC., Waterloo (CA)

(72) Inventors: Joseph Arthur Schipper, Kitchener (CA); Andre Novomir Hladio, Hamilton (CA); Kevin Morency, Guelph (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 230 days.

(21) Appl. No.: 15/919,777

(22) Filed: Mar. 13, 2018

(65) Prior Publication Data
US 2018/0263722 A1   Sep. 20, 2018

Related U.S. Application Data

(60) Provisional application No. 62/471,024, filed on Mar. 14, 2017.

(51) Int. Cl.
| | |
|---|---|
| *A61B 34/20* | (2016.01) |
| *A61B 90/00* | (2016.01) |
| *A61B 34/00* | (2016.01) |
| *A61B 90/94* | (2016.01) |
| *A61B 5/107* | (2006.01) |

(Continued)

(52) U.S. Cl.
CPC .............. *A61B 90/06* (2016.02); *A61B 5/107* (2013.01); *A61B 34/20* (2016.02); *A61B 34/25* (2016.02); *A61B 90/94* (2016.02); *G06V 20/64* (2022.01); *G06V 40/10* (2022.01); *A61B 2034/2048* (2016.02); *A61B 2034/2051* (2016.02); *A61B 2034/2055* (2016.02); *A61B 2034/256* (2016.02); *A61B 2090/061* (2016.02);
(Continued)

(58) Field of Classification Search
CPC ........... A61B 34/20–2034/258; A61B 17/8695
See application file for complete search history.

(56) References Cited

U.S. PATENT DOCUMENTS

| 9,603,665 B2* | 3/2017 | Bowling ................ A61B 34/30 |
| 2005/0203531 A1* | 9/2005 | Lakin ................... A61B 17/155 |
| | | 606/87 |

(Continued)

FOREIGN PATENT DOCUMENTS

WO         2014138910 A1      9/2014

*Primary Examiner* — Zade Coley

(57) ABSTRACT

There is provided a tracing platform configured to rigidly attach to an anatomy of a patient that has at least one surface configured to provide a defined path (represented by path definition data) for tracing by a surgical instrument. An intra-operative computing unit receives pose data for the instrument when tracing the path and calculates a location of the defined path using the pose data and the path definition data. A change in location may be determined from pose data of different traces. Tracing the defined path generates a plurality of pose data which may increase accuracy of the location calculations. Redundant trace data may be received to eliminate bias. A geometric feature (e.g. V-groove), shape and/or magnetic properties of the platform may assist with tracing. The platform may rigidly attach to a bone using at least one of spikes, a bone screw, a cerclage wire, and a bone clamp.

12 Claims, 8 Drawing Sheets

(51) Int. Cl.
  *G06V 20/64* (2022.01)
  *G06V 40/10* (2022.01)
  *G06V 10/62* (2022.01)
(52) U.S. Cl.
  CPC .......... *A61B 2505/05* (2013.01); *G06V 10/62* (2022.01); *G06V 2201/033* (2022.01)

(56) References Cited

U.S. PATENT DOCUMENTS

| | | | |
|---|---|---|---|
| 2006/0142657 A1* | 6/2006 | Quaid | A61F 2/30942 600/424 |
| 2011/0118742 A1* | 5/2011 | Hulliger | A61B 17/8047 606/70 |
| 2011/0182693 A1* | 7/2011 | Helgerson | A61B 17/7064 411/337 |
| 2014/0275940 A1* | 9/2014 | Hladio | A61B 5/1121 600/407 |
| 2015/0182292 A1* | 7/2015 | Hladio | A61B 34/20 606/87 |
| 2015/0297177 A1* | 10/2015 | Boctor | A61B 34/30 600/437 |
| 2017/0119475 A1* | 5/2017 | McCabe | A61B 5/066 |
| 2017/0189125 A1* | 7/2017 | Malackowski | A61B 34/20 |
| 2017/0265947 A1* | 9/2017 | Dyer | G16H 40/63 |
| 2019/0000372 A1* | 1/2019 | Gullotti | A61B 5/4566 |

* cited by examiner

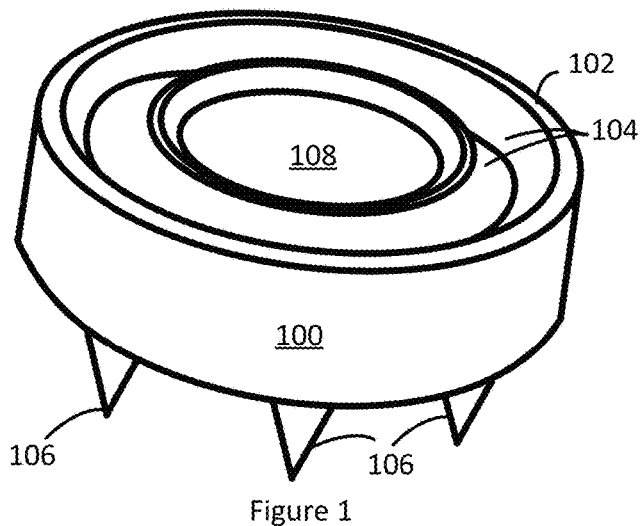
Figure 1
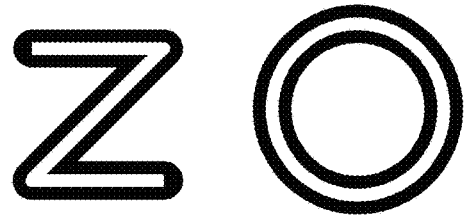
Figure 3A    Figure 3B
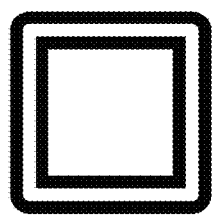 
Figure 3C    Figure 3D
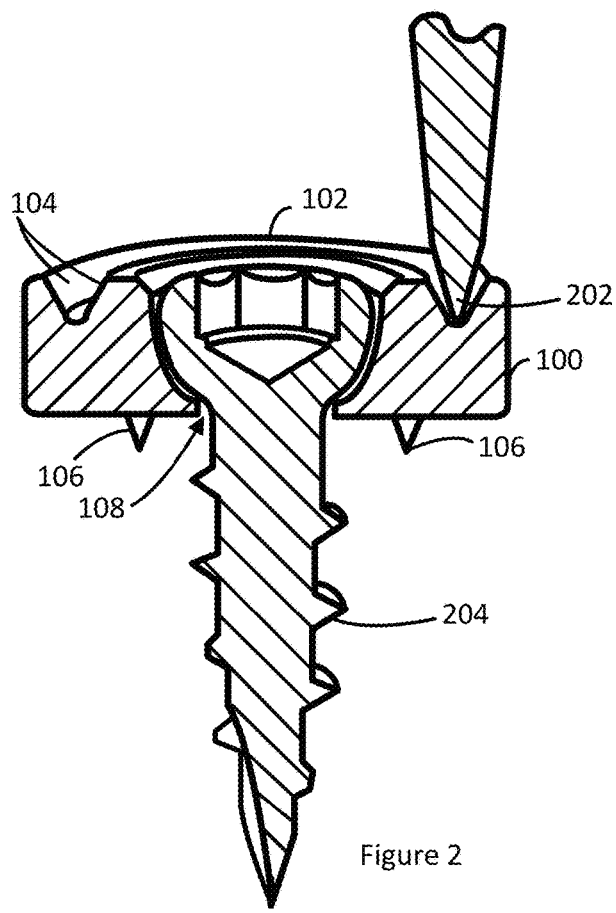
Figure 2
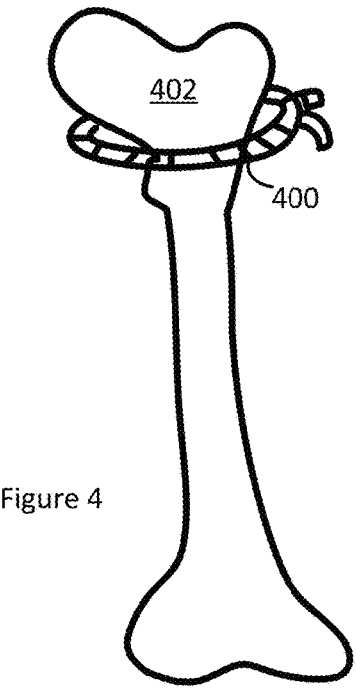
Figure 4

1300

TRACING PLATFORMS AND INTRA-OPERATIVE SYSTEMS AND METHODS USING SAME

CROSS-REFERENCE

The present application claims the benefit of U.S. Provisional Application No. 62/471,024 filed Mar. 14, 2017, the contents of which are incorporated herein by reference.

FIELD

The present specification relates to tracing platforms and intra-operative systems and methods using same to perform computer-assisted surgical procedures. For example, the tracing platforms and intra-operative systems and methods relate to determining a location and/or tracking a change in position and/or orientation of a rigid body in order to determine one or more surgical parameters such as a leg length during hip replacement surgery.

BACKGROUND

Tracking systems using various modalities such as optical, electromagnetic etc. are used in surgical procedures to obtain information about spatial localization of rigid bodies and the patient's anatomy. Pose data is captured (received at a computing unit) to determine poses of objects such as surgical instruments, patient anatomy, etc.

SUMMARY

There is provided a tracing platform to rigidly attach to an anatomy of a patient where the platform has at least one surface configured to provide a defined path for tracing by a surgical instrument. The defined path may be represented to a computing unit by path definition data. An intra-operative computing unit receives pose data for the instrument when tracing the path and calculates a location of the defined path using the pose data and the path definition data. A change in location may be determined from pose data of different traces. Tracing the defined path generates a plurality of pose data which may increase accuracy of the location calculations. Redundant trace data may be received to eliminate bias. A geometric feature (e.g. V-groove), shape and/or magnetic properties of the tracing platform may assist with the tracing. The tracing platform may rigidly attach to a bone using at least one of spikes, a bone screw, a cerclage wire, and a bone clamp.

In one aspect there is provided a tracing platform comprising: a body having at least one surface providing a defined path for tracing by a surgical instrument to generate pose data for the surgical instrument responsive to the defined path; and an attachment mechanism to rigidly attach the tracing platform to an anatomy of a patient. The defined path is associated with path definition data and wherein an intra-operative computing unit may receive the pose data for the surgical instrument responsive to the defined path and the path definition data and calculate a location of the defined path. The at least one surface may comprise a geometric feature to assist with the tracing by the surgical instrument. The path may be a closed path or an open path. The attachment mechanism may be one of spikes, a bone screw, a cerclage wire, and a bone clamp. The anatomy may be a femur and the surgical procedure a hip replacement surgery. The surgical instrument may be a probe.

In one aspect there is provided a system for intra-operative use during a surgical procedure, The system comprises: a tracing platform configured to rigidly attach to an anatomy of a patient and having at least one surface configured to provide a defined path for tracing by a surgical instrument, the defined path represented by path definition data; and an intra-operative computing unit configured to: obtain the path definition data related to the defined path; receive pose data from a tracking system related to the surgical instrument tracing the defined path; calculate a location of the defined path using the pose data and the path definition data; calculate a parameter based on the location of the defined path; and provide the parameter for display to a display unit.

The at least one surface may comprise a geometric feature (e.g. a V-groove) to assist with the tracing by the surgical instrument. The at least one surface may have magnetic properties to allow mating with a magnetic part of the surgical instrument. The at least one surface may have a shape to allow mating with a tip of the surgical instrument.

The anatomy may be a bone, and the tracing platform is configured to rigidly attach to the anatomy using at least one of spikes, a bone screw, a cerclage wire, and a bone clamp. The anatomy may be a femur and the surgical procedure a hip replacement surgery.

The defined path may be a closed path. The defined path may be a circle and the path definition data may be a radius of the circle.

The intra-operative computing unit may be configured to receive pose data comprising a redundant tracing of the defined path and to execute instructions to eliminate bias from the pose data.

The intra-operative computing unit may be further configured to validate pose data using the path definition data and to provide an error metric to the tracking system. The error metric may prompt a user of the tracking system to re-capture pose data of the defined path.

The intra-operative computing unit may be further configured to calculate a data metric using a quantity of pose data; and provide the data metric for display to a display unit.

The intra-operative computing unit may be further configured to receive additional pose data, and to calculate the parameter using additional pose data. The additional pose data may comprise landmark pose data corresponding to a landmark of the anatomy. The additional pose data may comprise pose data corresponding to a center of rotation of a joint of the anatomy.

The intra-operative computing unit may be further configured to receive pose data at a second instance of time to calculate a second location of the defined path and to further calculate a change in the location of the defined path and the second location of the defined path.

The intra-operative computing unit may be configured to display real-time receipt of valid pose data in the form of a progress bar.

The tracking system may be one of an optical tracking system and an electromagnetic tracking system. The pose data may correspond to a partial trace of the defined path. The surgical instrument may be a probe.

In an aspect there is provided a computer-implemented method comprising the steps of: obtaining, by at least one processing unit, path definition data related to a defined path on a tracing platform, the tracing platform configured to rigidly attach to an anatomy of a patient; receiving, by at least one processing unit, pose data from a tracking system related to a surgical instrument tracing the defined path; calculating, by at least one processing unit, a location of the defined path using the pose data and the path definition data; calculating, by at least one processing unit, a parameter based on the location of the defined path; and providing, by at least one processing unit, the parameter for display to a display unit.

In one aspect there is provided a system for intra-operative use during a surgical procedure, comprising: a tracing platform configured to rigidly attach to an anatomy of a patient and having at least one surface configured to provide a defined path for tracing by a surgical instrument; and an intra-operative computing unit configured to: obtain path definition data related to the defined path; receive first pose data at a first instance of time from a tracking system related to the surgical instrument tracing the defined path and first landmark pose data corresponding to a landmark of the anatomy; calculate a first location of the defined path using the first pose data, the first landmark pose data and the path definition data; receive second pose data at a second instance of time from a tracking system related to the surgical instrument tracing the defined path and second landmark pose data corresponding to the landmark of the anatomy; calculate a second location of the defined path using the second pose data, the second landmark pose data and the path definition data; receive additional pose data corresponding to a joint of the anatomy; calculate a parameter using a change in the first location of the defined path and the second location of the defined path, and additional pose data; and provide the parameter for display to a display unit.

In one aspect there is provided a computer-implemented method for intra-operative use during a surgical procedure, comprising the steps of: obtaining, by at least one processing unit, path definition data related to a trace of a defined path on at least one surface of a tracing platform, the tracing platform configured to rigidly attach to an anatomy of a patient; receiving, by at least one processing unit, first pose data at a first instance of time from a tracking system related to the surgical instrument tracing the defined path and first landmark pose data corresponding to a landmark of the anatomy; calculating, by at least one processing unit, a first location of the defined path using the first pose data, first landmark pose data corresponding to a landmark of the anatomy and the path definition data; receiving, by at least one processing unit, second pose data at a second instance of time from a tracking system related to the surgical instrument tracing the defined path and second landmark pose data corresponding to the landmark of the anatomy; calculating, by at least one processing unit, a second location of the defined path using the second pose data, the second landmark pose data and the path definition data; receiving, by at least one processing unit, additional pose data comprising pose data corresponding to a center of rotation of a joint of the anatomy; calculating, by at least one processing unit, a parameter using a change in the first location of the defined path and the second location of the defined path, and the additional pose data; and providing, by at least one processing unit, the parameter for display to a display unit.

These and other aspects such as a computer program product aspect will be apparent to those of ordinary skill in the art. A computer program product may comprise a computer readable medium (e.g. a storage device) storing instructions in a non-transient manner, which instructions, when executed by at least one processing unit, configure an intra-operative computing device to perform any of the method aspects herein.

BRIEF DESCRIPTION OF THE DRAWINGS

Drawings are included in which:

FIG. 1 is a top perspective view of a tracing platform in accordance with an example;

FIG. 2 is a cross-sectional side view showing the tracing platform of FIG. 1 together with a bone screw to mount the tracing platform and a probe tip in a groove of the tracing platform showing use;

FIGS. 3A, 3B, 3C and 3D are illustrations of example paths (shapes) which may be provided by a tracing platform;

FIG. 4 is an illustration of a bone clamp on a femur;

DETAILED DESCRIPTION

Figure 5:
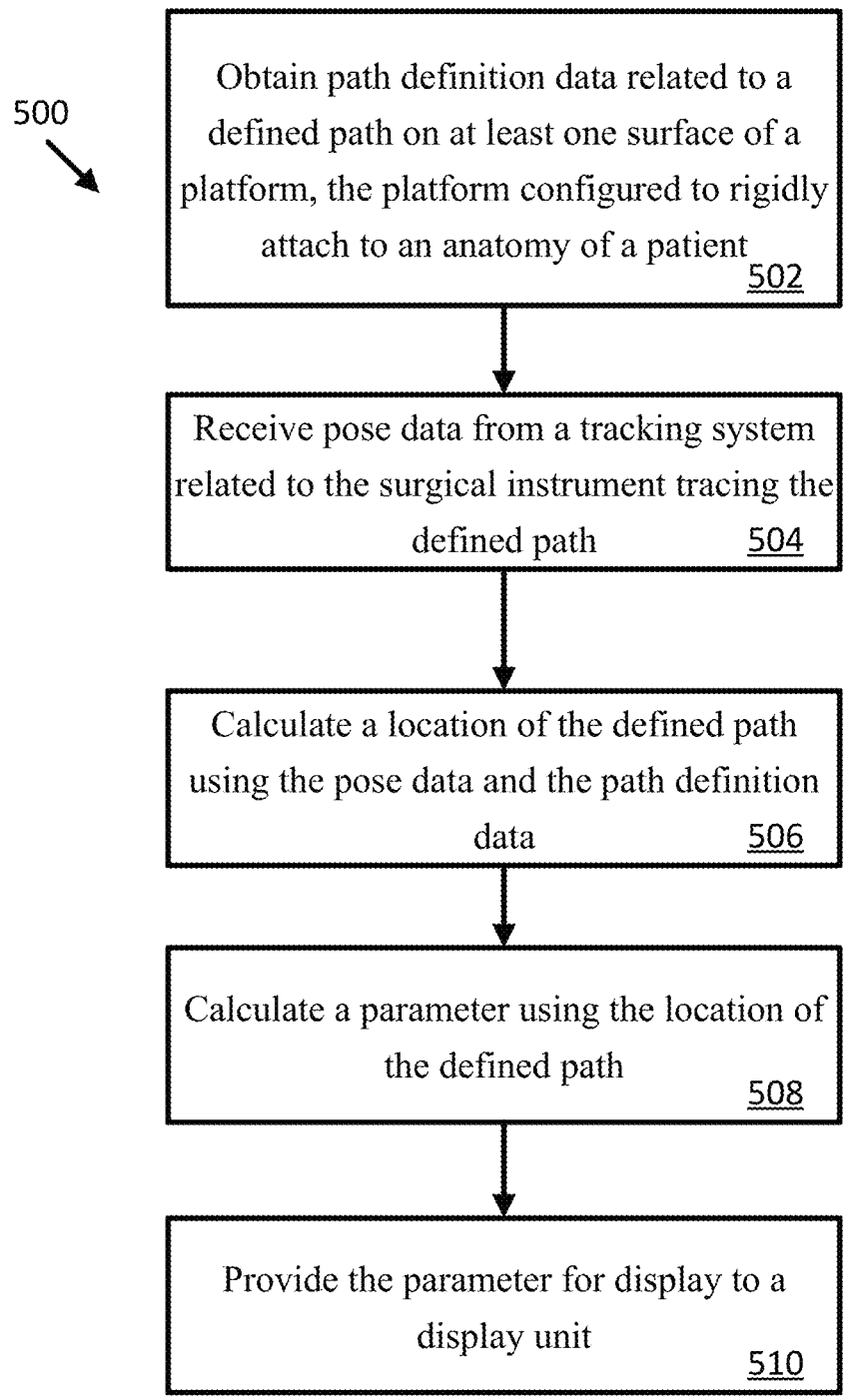
FIG. 5 is a flow chart of operations of an intra-operative computing device according to an example.

Reference in the specification to "one embodiment", "an embodiment", or "embodiments" means that a particular feature, structure, characteristic, or function described in connection with the embodiment is included in at least one embodiment, and may be in more than one embodiment or each of the embodiments. Also, such phrases in various places in the specification are not necessarily all referring to the same embodiment or embodiments.

A computing unit may comprise a laptop, workstation, or other computing device having at least one processing unit and at least one storage device such as memory storing software (instructions and/or data) as further described herein to configure the execution of the computing unit.

A tracking system provides spatial localization of a rigid body (such as, instruments, implants, anatomical structures etc.) with respect to another rigid body (such as, another instrument, a patient's anatomy etc.). Examples of tracking systems and associated methods are described in greater detail in WO2014/138910 A1 published Sep. 18, 2014 and titled "System and Method for Intra-operative Leg Position Measurement" by Hladio et al, the entire contents of which are incorporated herein by reference. Tracking systems may have various modalities such as, optical, electromagnetic and may use active or passive trackers to provide pose (position and orientation) data of the rigid body being tracked. The present specification describes embodiments that are agnostic to the modality of a tracking system.

A system is disclosed herein for intra-operative use during a surgical procedure, comprising a tracing platform configured to rigidly attach to an anatomy of a patient and having at least one surface configured to provide a defined path for tracing by a surgical instrument, and an intra-operative computing unit configured to obtain path definition data related to the defined path, receive pose data from a tracking system related to the surgical instrument tracking the defined path, calculate a location of the defined path using the pose data and the path definition data; calculate a parameter based on the location of the defined path, and provide the parameter for display to a display unit. FIG. 1 is a top perspective view of tracing platform in accordance with an example. FIG. 2 is a cross-sectional side view showing the tracing platform of FIG. 1 together with a bone screw to mount the tracing platform and a probe tip in a groove of the tracing platform showing use.

The path definition data may be pre-loaded into the computing unit and may correspond to geometrical properties of the defined path. For example, the defined path may be of an expected shape such as, a circle or a square, and the path definition data may describe certain geometrical properties of the shape such as, radius or length of side.

The pose data is provided by a tracking system. The tracking system may be distinct or integrated with the system described herein. The pose data may be captured in real-time by a tracking system and provided to the system disclosed herein. The pose data may be captured while a user is tracing the defined path using a surgical instrument such as a probe with a tip. Tracing the defined path, in this specification, means that the surgical instrument is used to continuously move along while making contact with multiple points on the defined path. The pose data corresponding to each point is then provided to an intra-operative computing unit of the system herein to calculate a location of the defined path.

The location is calculated by using the pose data and the path definition data corresponding to the defined path. This location could be in a spatial coordinate system that is specific to the tracking system, or alternatively it could be in an arbitrary spatial coordinate system. The location of the defined path is further used to calculate a parameter for intra-operative use. For example, the parameter may be a surgical measurement such as spatial information (in up to 6 degrees of freedom) corresponding to a femur bone in total hip arthroplasty or revision hip replacement. The parameter is then displayed to a display unit.

As further shown and described with reference to FIGS. 1 and 2, a tracing platform 100 (sometimes referenced more succinctly as "platform") comprises a body having at least one surface providing the defined path for tracing by a surgical instrument such as a probe. The tracing platform 100 may be manufactured from a medical grade material that is biocompatible and has appropriate mechanical characteristics for tracing. This material includes titanium and stainless steel. The at least one surface may have a geometric feature to assist with tracing such as by a tip of a surgical instrument. For example, surface 102 of tracing platform 100 provides a geometric feature in the form of contours 104 defining one or more channels and/or one or more apertures (not shown) defining one or more slots for receiving a tip 202 of a surgical instrument (not shown) to guide the tip 202 along the defined path of the channel(s) and/or slot(s) defined by contours 104. FIGS. 1 and 2 show tracing platform 100 with a geometric feature that is designed to assist with tracing by the surgical instrument, for example, with the tip 202 of the probe, the cross-section of which geometric feature is in the shape of the letter "V".

In cross-section, the shape of the channel defined by the contours 104 may be V-shaped to receive a like shaped tip 202 of a probe (surgical instrument). In addition, the geometric feature may also be designed to be magnetic, and the corresponding surgical instrument to have a magnetic component that mates with the geometric feature to enable a user to steadily trace the defined path. FIG. 2 shows a cross-section of tracing platform 100 with a circular defined path and highlights the tip 202 of the probe that mates with the V-groove such that the tip 202 has a consistent position with respect to the geometrical feature throughout a trace of the defined path.

FIGS. 3A-3D are illustrations of example paths (shapes) which may be provided by a tracing platform. Any one platform may only have one defined path to avoid confusing user but any platform may have more than one. FIG. 3A shows a defined path in the shape of the letter "Z". Other defined paths, for example, a circle (FIG. 3B), a square (FIG. 3C), a triangle (FIG. 3D) or any other geometrical shape such as a letter of the alphabet are also contemplated. While this specification refers to the use of planar defined paths, it is contemplated that non-planar defined paths can be used. For example, a hemi-spherical surface may provide a defined path for tracing.

The defined path may be closed i.e. the starting point of a trace may coincide with the end point of the trace. Closed path examples include a circle, an oval, a square, a rectangle, etc. Open paths have a starting point of the trace that does not coincide with the end point of the trace. Open paths may be Z-shaped, U-shaped, X-shaped, C-shaped, etc. (where U, X and C are not shown). A closed defined path may allow a user to perform redundant tracing of the defined path. This may be a beneficial feature of usability for a user. Redundant tracing may also be possible in an open defined path such as by reversing the trace. FIGS. 3B-3D represent closed paths. While a user performs redundant tracing, the intra-operative computing unit may retain pose data it receives from the tracking system for comparison/error detection. It may be configured to execute error mechanisms that remove bias in the results due to unequal collection and/or weightage to pose data from different sections of the defined path, for example, by averaging weightage of pose data from different sections of the defined path.

The tracing platform may be configured to rigidly attach to the anatomy such as a bone, using various attachment mechanisms. For example, the platform shown in FIGS. 1 and 2 has spikes 106 that can be used to attach the platform to a surface of the patient's anatomy. In addition, it is contemplated that a bone screw 204 may be used to attach the platform as shown in FIG. 2. Tracing platform 100 may define an aperture 108 to receive the bone screw 204. FIG. 4 is an illustration of a bone clamp 400 on a femur 402. It may also be feasible to attach the platform 100 to the anatomy using a cerclage wire (not shown) or the bone clamp 400 such as to femur 402.

The tracing platform and the attachment mechanism (e.g. screw, wire or clamp, etc.) may be distinct or may be integrally formed. Various attachment mechanisms are contemplated to allow use of the system disclosed herein in different types of surgical procedures where a surgeon is operating on anatomy that may not provide sufficient space to attach a tracing platform. The tracing platform may be sized according to dimensions of such attachment mechanisms.

FIG. 5 illustrates a flowchart of operations 500 showing the different steps of the method described above as performed by an intra-operative computing unit (e.g. a component of a surgical navigation system or an object tracking system) having at least one processing unit. At 502, operations obtain, by at least one processing unit, path definition data related to a trace of a defined path on at least one surface of a platform, the platform configured to rigidly attach to an anatomy of a patient. At 504, operations receive, by at least one processing unit, pose data from a tracking system related to the surgical instrument tracing the defined path. At 506, operations calculate, by at least one processing unit, a location of the defined path using the pose data and the path definition data. At 508, operations calculate, by at least one processing unit, a parameter using the location of the defined path. And at 510, operations provide, by at least one processing unit, the parameter for display to a display unit.

The location of the defined path may change within a coordinate system during the surgical procedure. In order to calculate a change in the location of the defined path, the computing unit may use pose data from different traces generated at two or more instances of time. For example, the computing unit may calculate a first location of the defined path pre-dislocation of a joint and a second location may be calculated post-reduction of the joint after a surgical procedure. The difference between the first location and the second location would correspond to a change due to the surgical procedure, expressed by a parameter. Alternatively, calculation of a first location may be sufficient for some applications of the system herein. For example, in revision hip replacement where a part of the femoral bone is removed during the surgical procedure, it may only be feasible to obtain a first location of the defined path.

Depending on the configuration, the system may also be able to accept pose data corresponding to a partial trace of the defined path to calculate a location of the defined path.

Additional pose data from the tracking system may also be used by the system described herein to calculate the parameter, or other relevant parameters for the surgical procedure. For example, the tracking system may provide additional pose data corresponding to a joint center of rotation and/or landmark pose data corresponding to an additional landmark on the anatomy (e.g. distal point on femur, ASIS (anterior superior iliac spine) on pelvis etc.). In such an example, the system can use the additional pose data, landmark pose data, pose data and path definition data to calculate a location of the defined path of the platform. A larger set of information in the pose data will improve accuracy of the location of the defined path.

Additional systems and methods to obtain pose data related to joint center of rotation and/or an additional landmark is available in U.S. Publication No. 2017/0119475 A1, published May 4, 2017, and titled "SYSTEMS, METHODS AND DEVICES FOR CALCULATING HIP CENTER OF ROTATION, ADJUSTING PARAMETERS OF JOINT REPLACEMENT FOR PELVIC TILT AND CALCULATING LEG LENGTH AND OFFSET" by McCabe et al, the entire contents of which are incorporated herein by reference.

Due to the large number of poses captured in the pose data from the tracking system, this method provides more accurate results than pose data calculated with a smaller number of poses. In addition, error checking mechanisms may be implemented by the system herein. Such error mechanisms are described in greater detail in U.S. Publication No. 2017/0119475 A1 and further in this specification. For example, an invalid pose in the pose data may be captured when the user's hand slips or moves during the trace. The instructions on the computing unit may execute such that a trace of the defined path from the tracking system will not be accepted until a minimum number of valid poses are received or will indicate to the tracking system to restart the process of capturing pose data when slippage is detected. Feedback to the user of the tracking system may be provided in the form of a counter, or a progress bar indicating the capture of valid poses displayed on a display screen such that a user is unable to bypass this step until an appropriate set and/or number of poses is captured.

Description of Exemplary Application

Figure 6:
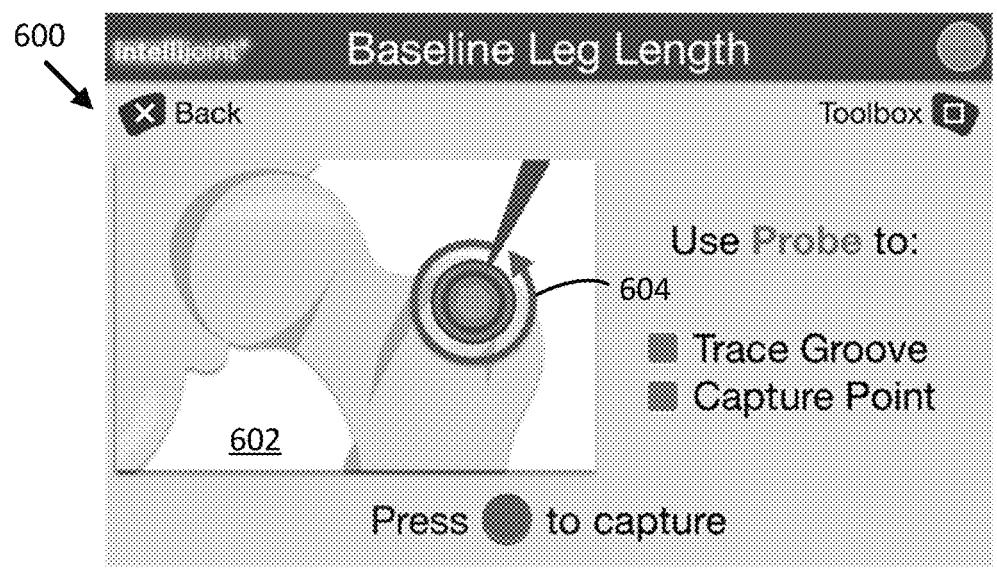
FIGS. 6 and 7 are screen shots of a graphical user interface according to an example showing workflow and information for an example procedure.
Figure 7:
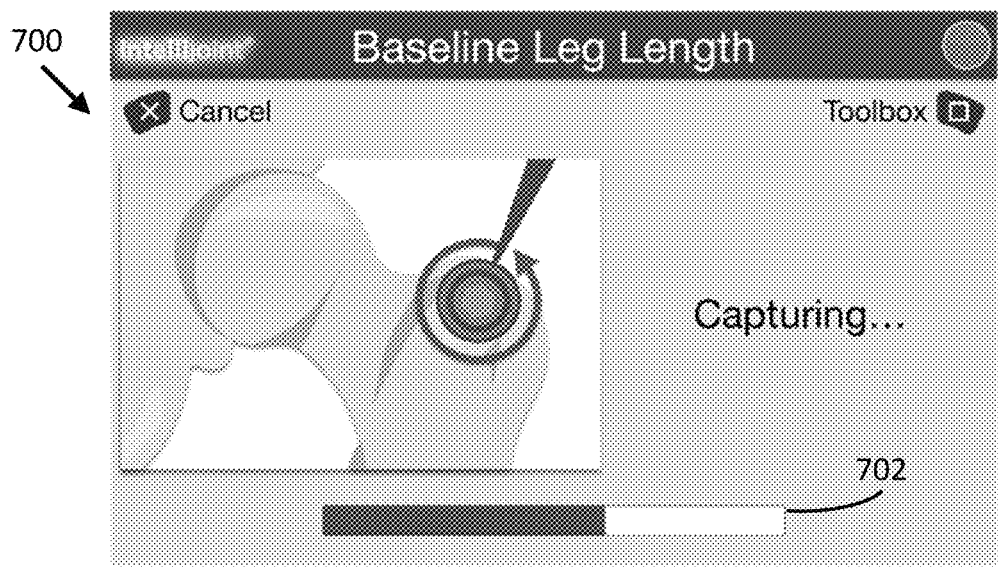

An exemplary application of the system described herein is provided below described in the context of a total hip arthroplasty surgical procedure. The system uses a platform that comprises a surface providing a circular defined path. The platform is attached to a femur of a patient using spikes and a bone screw. The computing unit loads path definition data corresponding to the circular defined path. The computing unit may then receive real-time pose data from a tracking system that is tracking a probe as the probe (though its tip) traces the defined path. FIGS. 6 and 7 show exemplary GUI screenshots 600 and 700 providing workflow directions that correspond to collection of pose data through the tracking system. Pose data may be collected at two instances of time—baseline and current. This allows the computing unit to calculate a change in parameter of leg length and offset for hip replacement surgery. FIG. 6 shows a GUI providing prompts to initiate a capture including a graphical representation 602 of the platform mounted to a femur and graphic directions 604 to trace the defined path on the platform with tip of a probe. FIG. 7 shows a GUI including a progress bar 702 indicating a progress of the capture of poses generated by the trace of the defined path of the platform using the tip of the probe. It is understood that the probe has trackers (e.g. sensors which may be passive or active) for tracking by a sensor data tracking component according to the modality of the system. For example the trackers may be optical sensors to generate or reflect light and the sensor data tracking component may be a camera capturing optical signals (light) from the optical sensors.

The computing unit may execute instructions to implement mechanisms to ensure that sufficient (in terms of accuracy and quantity) pose data is captured in real-time. By way of example, pose data comprising a minimum of 60 poses may be required, spread out substantially equally over various sections of the defined path. With a frame rate of 30 frames/second, the computing unit may execute instructions to only collect poses as the surgical instrument is moved along the defined path, etc.

The validity of the pose data may be determined, in part, by the path definition data related to the defined path. For example, in this application, the defined path is expected to lie along a circumference of a circle, the pose data may be expected to yield points that approximately correspond to a circle with a known radius. Error checking mechanisms may be used to provide user prompts to the tracking system through a graphical user interface (GUI) as guidance to a user during this step.

Figure 8:
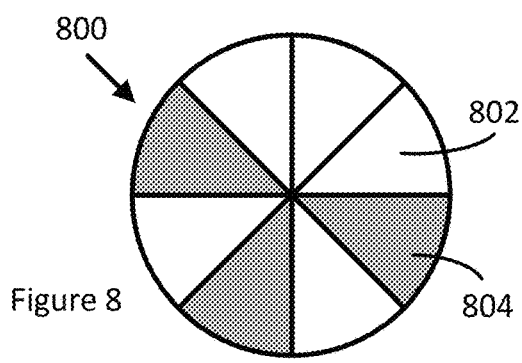
FIG. 8 is an illustration of a progress indicator component of a graphical user interface according to an example.

In addition, the user may also be provided with data metrics (such as, quantity of pose data) during the trace to guide the user to trace a given area of the defined path. For example, as illustrated in FIG. 8 where an example graphical element of a GUI is shown, if the defined path is circular, a circle 800 may be divided into smaller pie sections (e.g. 802 and 804) or bins. These sections may be color coded and displayed on the GUI such as a GUI 700. As the computing unit receives real-time pose data sufficient to cover each pie section or bin of the circle, the user of the tracking system may be notified by a change in color or other similar indication.

Figure 9:
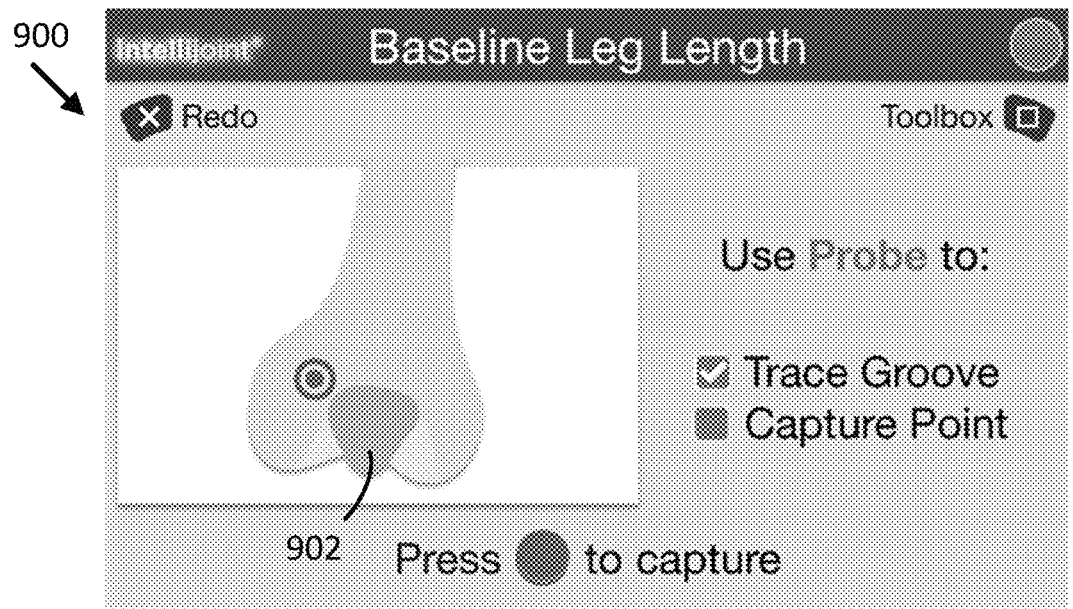
FIGS. 9-13 are screen shots of a graphical user interface according to an example showing workflow and information for an example procedure.
Figure 10:
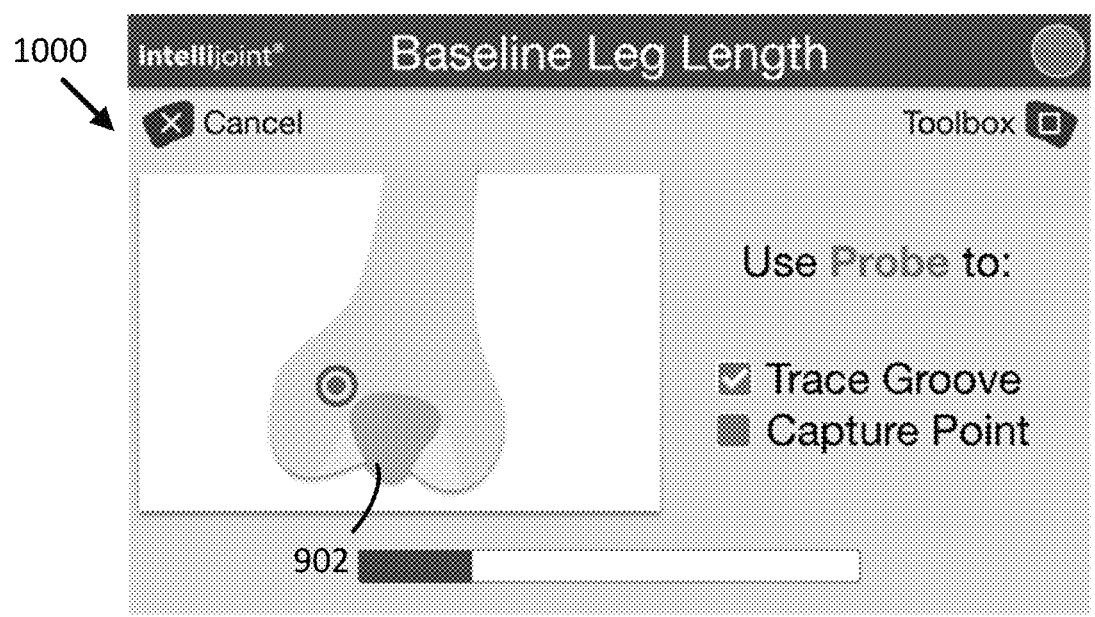

The tracking system may also provide landmark pose data corresponding to a distal point on the femur. The user of the tracking system is prompted to probe a distal point 902 to obtain landmark pose data as shown in FIGS. 9 and 10 showing GUI screenshots 900 and 1000 providing workflow to determine a baseline leg length. Using the pose data, landmark pose data and the path definition data, the intra-operative computing unit of the system herein calculates a location of the circular defined path in accordance with example computations described further in this specification.

Figure 11:
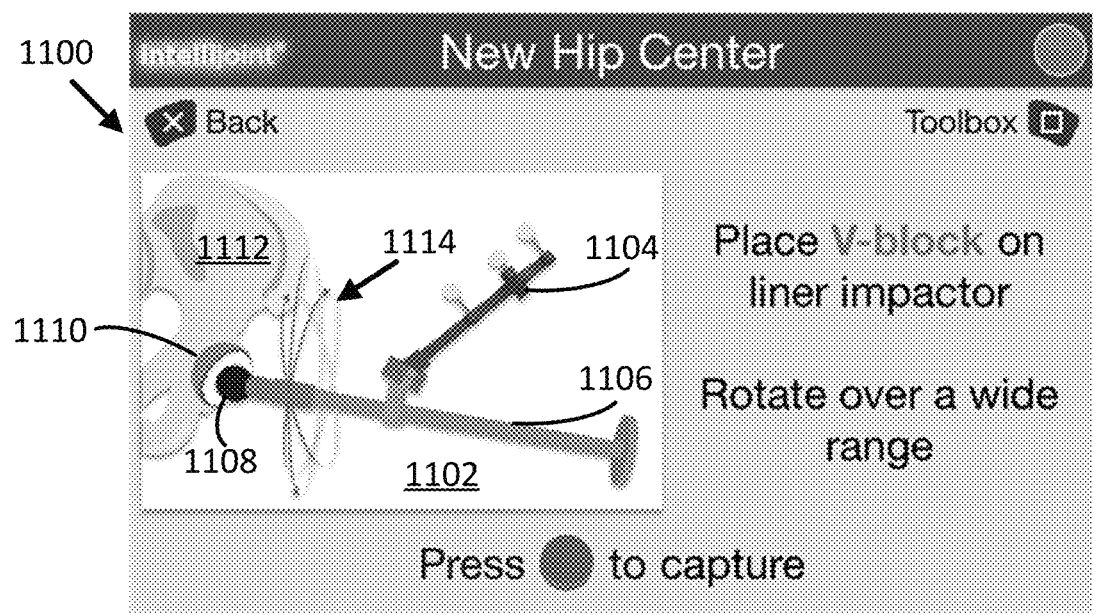
Figure 12:
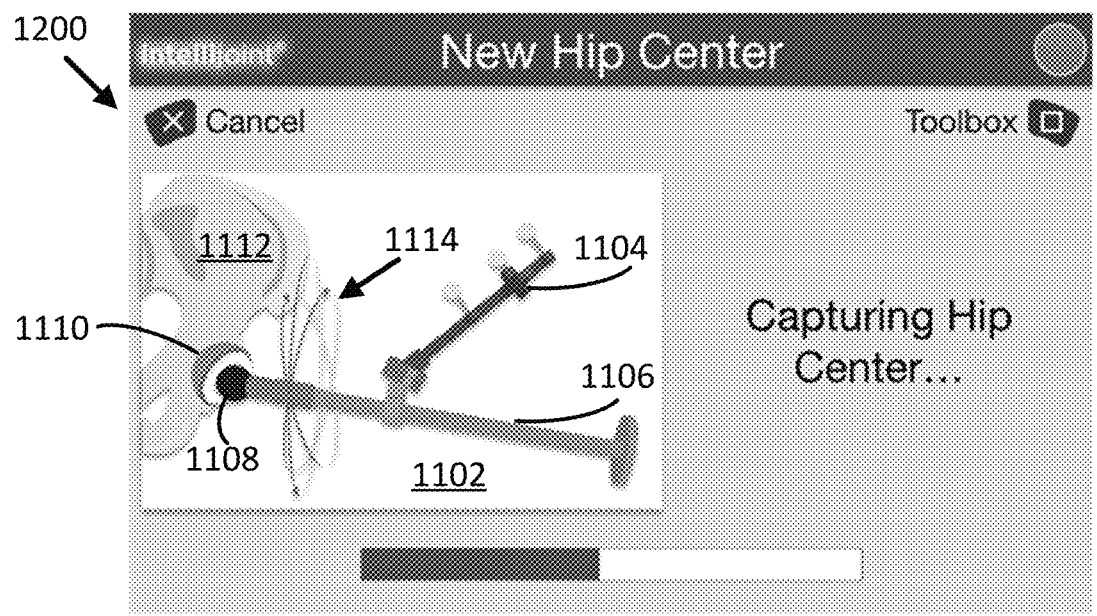

The joint center of rotation may be calculated by methods described in U.S. application Ser. No. 15/337,409. In this example, a post-reduction joint center of rotation are captured by the tracking system as shown in FIGS. 9 and 10 and FIGS. 11 and 12. FIGS. 11 and 12 are GUI screenshots 1100 and 1200 showing workflow steps to capture a post reduction joint center of rotation. GUIs 1100 and 1200 show a graphical representation 1102 of a tracker 1104 coupled to a surgical instrument 1106 (liner impactor) where a head 1108 of the surgical instrument 1106 is positioned within an acetabular cup 1110 in a pelvis 1112. Graphical representation 1102 includes arrows and other movement signs 1114 to direct a (rotational) movement of the surgical instrument 1106 to generate pose data.

Using the additional pose data corresponding to the joint center of rotation, the computing unit of the system herein further calculates and provides to a display unit a change in location of the defined path about the post-reduction joint center of rotation.

The following equations describe example instructions executing on the computing unit for this exemplary application:

Using N points corresponding to the received pose data:

$$X = [\,p^1 \ \ldots \ p^N\,],$$

where $N > 3$ $$p^i = \begin{bmatrix} p_x^i \\ p_y^i \\ p_z^i \end{bmatrix}$$

The instructions then use algebraic methods to calculate $\hat{n}$, a unit vector that points in a positive Z-direction of a coordinate frame (for example, coordinate frame of the tracking system). The $\hat{n}$ vector is normal to the set of points captured in X and is used to calculate a rotation matrix R such that the normal vector $\hat{n}$, is coincident with the positive Z-direction of the coordinate frame.

$$\begin{bmatrix} x^T \\ y^T \\ z^T \end{bmatrix} = RX$$

Solve for the circle center c and radius r using the x, y, and z points above:

$$A = [2x \ 2y \ 1],$$
$$b = x^2 + y^2,$$

where $A = \begin{bmatrix} X \\ 1 \end{bmatrix} = \begin{bmatrix} p^1 & \ldots & p^N \\ 1 & \ldots & 1 \end{bmatrix}$ $$\begin{bmatrix} c_x \\ c_y \\ r^2 - (c_x^2 + c_y^2) \end{bmatrix} = (A^T A)^{-1} A^T b$$

$$c_z = z$$

Implement error mechanisms to verify the value of the calculated radius using the known radius from the path definition data for validation. While pose data is collected, the error for a current set of points is calculated as follows:

for $i = [\,1 \ \ldots \ N\,]$ $err_{zi} = z_i - c_z$ $err_{ri} = \sqrt{(x_i - c_x)^2 + (y_i - c_y)^2} - r$ $err_i^2 = err_{zi}^2 + err_{ri}^2$ $\phi_i = \tan 2^{-1}(x_i, y_i) + \pi$ $j = \left\lfloor \dfrac{M \phi_i}{2\pi} \right\rfloor$ for $M$ bins, where bins correspond to pie sections shown in FIG. 8.
Insert $err_i^2$ into $bin_j$.
Calculate the final error:

$$err = \sqrt{\dfrac{1}{M} \sum_{j=1}^{M} \overline{bin_j}}$$

where $\overline{bin_j}$ is the mean of all $err_i^2$ inserted into $bin_j$.

If the final error is above a certain threshold, the computing unit can execute instructions to either discard the pose and/or prompt the tracking system to continue collection of pose data.

Further, the computing unit solves for a translation component for the center of the circle:

$t = R^T c$

Calculate a leg rotation matrix RL, using landmark pose data for $p_{dist}$, a distal point on the femur.

$RL = [\,v_x \ v_y \ v_z\,]$ $v_z = \hat{n}$ $v_y = \dfrac{v_z \times (p_{dist} - t)}{\|v_z \times (p_{dist} - t)\|}$ $v_x = v_y \times v_z$ Using additional pose data corresponding to a joint hip center of rotation to virtually re-orient the leg back to the position in which a first baseline location was calculated for the leg:

$p'_{current} = R_{baseline} R_{current}^T (p_{current} - p_{newCOR}) + p_{newCOR}$ $\Delta leg = (R_P^C)^T (p'_{current} - p_{baseline})$ Where, the baseline pose is a first location of the defined path, and the current pose is a second location of the defined path.

$R_{baseline}$—The rotation matrix for the orientation part of the baseline pose.

$p_{baseline}$—The translation vector for the position part of the baseline pose.

$R_{current}$—The rotation matrix for the orientation part of the current pose.

$p_{current}$—The translation vector for the position part of the current pose $p'_{current}$ The translation vector representing the location of the tracker after being "virtually re-oriented" to the same orientation as the baseline pose.

Figure 13:
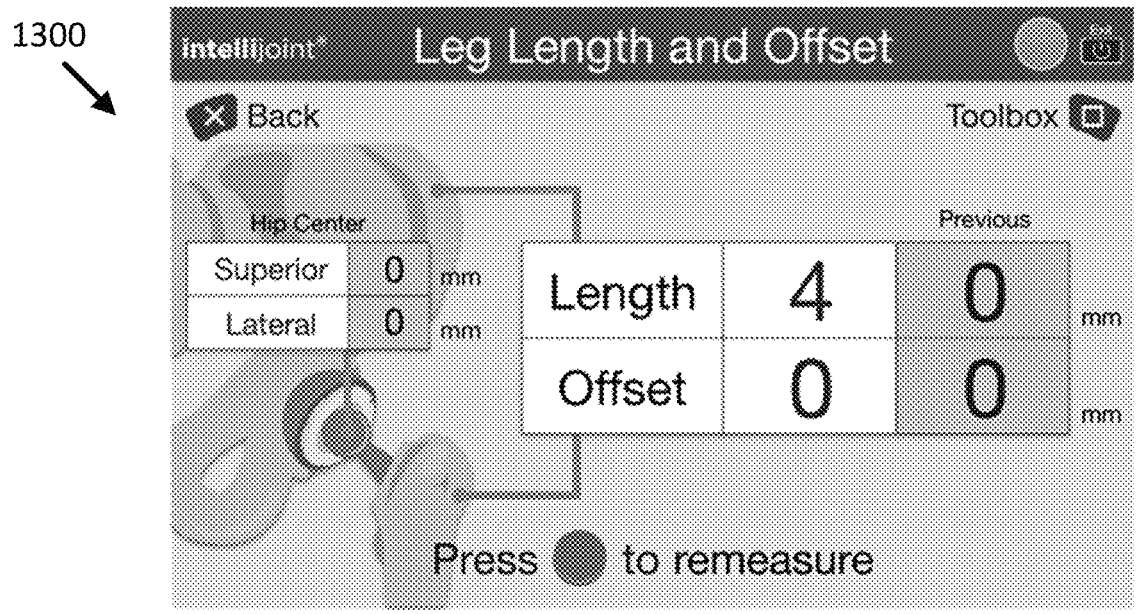

The change in leg length and offset are the parameters displayed to a display unit in a GUI such as depicted in screenshot 1300 of FIG. 13.

Figure 14:
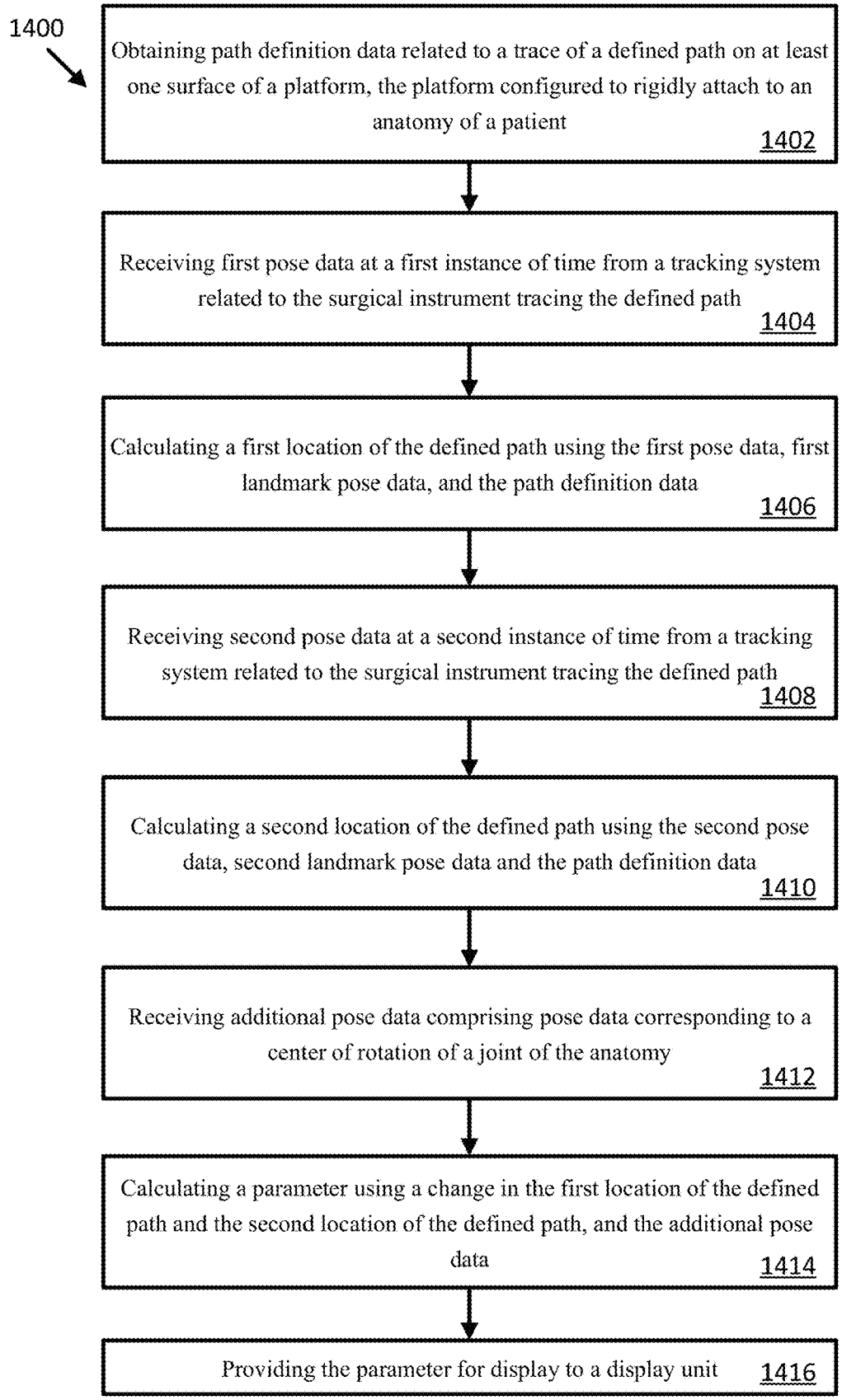
FIG. 14 is a flowchart of operations of an intra-operative computing device according to an example.

FIG. 14 is a flowchart of operations 1400 showing an example method to determine a parameter using a change in location of the defined path. At 1402 operations obtain, by at least one processing unit, path definition data related to a trace of a defined path on at least one surface of a platform, the platform configured to rigidly attach to an anatomy of a patient. At 1404 operations receive, by at least one processing unit, first pose data at a first instance of time from a tracking system related to the surgical instrument tracing the defined path. At 1406 operations calculate, by at least one processing unit, a first location of the defined path using the first pose data, first landmark pose data, and the path definition data. At 1408 operations receive, by at least one processing unit, second pose data at a second instance of time from a tracking system related to the surgical instrument tracing the defined path. At 1410 operations calculate, by at least one processing unit, a second location of the defined path using the second pose data, second landmark pose data and the path definition data. At 1412 operations receive, by at least one processing unit, additional pose data comprising pose data corresponding to a center of rotation of a joint of the anatomy. At 1414 operations calculate, by at least one processing unit, a parameter using a change in the first location of the defined path and the second location of the defined path, and the additional pose data. At 1416 operations provide, by at least one processing unit, the parameter for display to a display unit.

Figure 15:
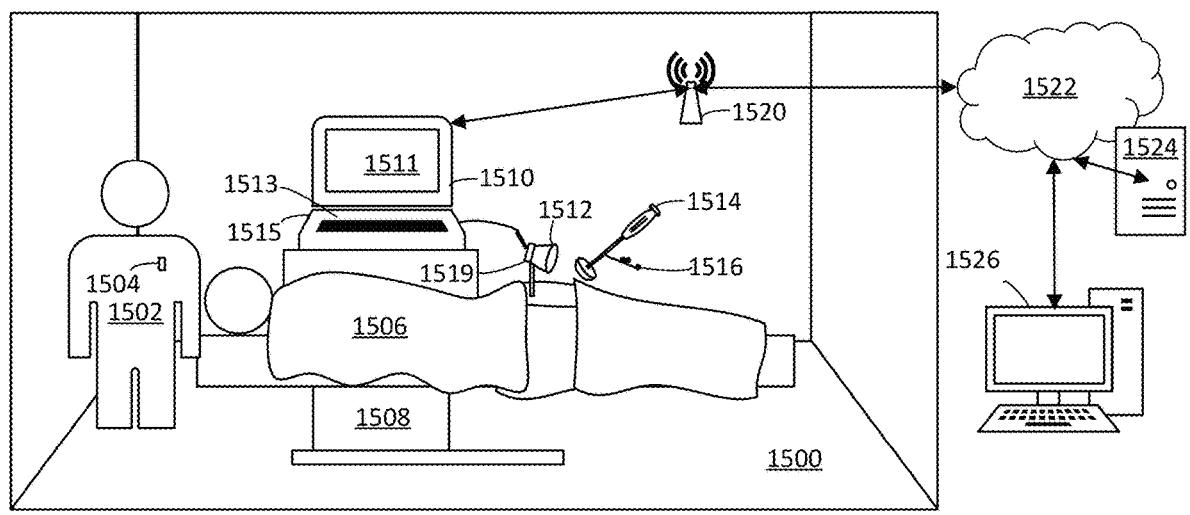
FIG. 15 is a diagram of an intra-operative computing system in an operating room.

FIG. 15 shows an intra-operative computing system in an operating room (OR) coupled to a network and other computing systems external to the OR according to an example. It is understood that the intra-operative computing system need not be coupled to a network. FIG. 15 shows OR 1500 in which a surgeon 1502 or other person is attending in OR 1500. It will be appreciated that for many types of procedures that many persons including additional surgeons or other doctors (e.g. anesthesiologists), nurses, etc., may be attending (not shown) and that only some of the OR equipment is shown. Surgeon 1502 is wearing a wireless microphone 1504. A patient 1506 is on an OR table 1508. OR table 1508 (or a cart (not shown)) may be configured with a suitable support for an OR computing device 1510 comprising at least one processing unit coupled to a display device 1511 and a data store 1515 (e.g. memory or other storage device). Wireless microphone 1504 may be coupled communicatively to OR computing device 1510. OR computing device 1510 may have other input/output or IO devices, for example a display device 1511, a keyboard 1513, and a pointing device (e.g. mouse), among others.

In FIG. 15, OR computing device 1510 is coupled to or is a component of a localization system for tracking objects during a computer-assisted procedure. Localization system may be optically based and comprise an OR camera 1512 (a type of sensor) for tracking an object 1514 such as a surgical instrument 1516 as shown, a part of a patient (e.g. a bone), or any other object whose pose is desired. Object 1514 has an optical tracker 1516 (type of sensor) for use to indicate a pose of object 1514. OR camera 1512 may be mounted on a bone of the patient as shown or on a boom (not shown), a component of OR table 1508 (not shown) or a standalone unit having wheels (not shown), etc. It may be mounted to a ceiling or other surface of the OR 100A (not shown).

Optical tracker 1516 may be selectively removable (for example to couple to a different object (not shown)) for the procedure. Optical tracker 1516 may be passive and reflect light or active and originate light for detection and/or measurement by OR camera 1512. OR camera 1512 may be a stereo camera set-up or other configuration. Optionally OR camera 1512 may provide high resolution video signals (e.g. video data) in a visible light spectrum to OR computing device 1510 to visualize at least a portion of the OR 1500. OR camera 1512 may provide object tracking signals (e.g. sensor data), for example tracking optical tracker 1516 in an infrared (IR) spectrum or other spectrum.

In at least some examples, OR camera 1512 may have one or more gravity sensors 1519 configured to measure gravity (e.g. accelerometers/inertial sensors) to indicate the direction of gravity relative to the object to which it is attached. Such gravity sensors 1519 or optical trackers 1516 may be attached to any object in the OR 1500 including patient 1506 to provide a reference to a patient to determine pose information (though in practice attaching to OR table 1508 may be sufficient to indicate the position of the patient). It will be understood that OR camera 1512 may only track optical trackers 1516 when optical trackers 1516 are in a field of view of OR camera 1512, which field of view is typically directed towards a treatment site relative to patient 1506. Though not shown, one or more video cameras providing video data may be coupled to OR computing device 1510, for example, should OR camera 1512 not provide video data and be restricted to providing sensor data.

OR computing device 1510 is coupled via a communication system (e.g. a component of OR computing device 1510) to communicate to other computing devices via a network. Shown in OR 1500 is a wireless access point 1520 for communicating via a public communication network 1522 such as the Internet. OR computing device 1510 may be configured for wire based communication to other computing devices, including those external to the OR. Such other computing devices may be servers or other systems (e.g. Picture Archival and Communication Systems (PACs) storing pre-operative (pre-op) data for a patient such as patient information, reports and clinical images (e.g. Magnetic Resonance Imaging (MRI), X-Ray, or images from other modalities). Some of these servers or systems may be located geographically remote from the OR 1500 or more closely such as in a same hospital (not shown).

Wireless access point 1520 may be located externally to the OR 1500. It will be appreciated that other communication components may be used (e.g. routers, firewalls, etc.) and that the network components in FIG. 15 are simplified. OR computing device 1510 may communicate with a server 1524 (or more than one), which may store pre-op data for a patient, geometric definitions of objects to be tracked, etc. Server 1524 may provide services to share OR data (e.g. streamed video, etc.) to monitor the OR 1500A to a monitoring computing device 1526. Server 1524 (or another server) and monitoring computing device 1526 may define a monitoring computing system.

OR computing device 1510 and any localization system with which it is coupled in OR 1500 are examples of respective OR computing systems configured for surgical navigation. Each OR computing system comprises one or more computing units to perform a computer-assisted procedure relative to a patient. Each tracks respective positions of one or more objects during the procedure in the operating room. Sensor data, representing the respective positions of the one or more objects, is received from sensors associated with the one or more objects. Typically the association is provided by coupling a one of the respective sensors to the object. Some additional sensors and or data may be used.

Accordingly, it is to be understood that this subject matter is not limited to particular embodiments described, and as such may vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the teachings herein. Any recited method can be carried out in the order of events recited or in any other order which is logically possible.

Various embodiments have been described herein with reference to the accompanying drawings. It will, however, be evident that various modifications and changes may be made thereto, and additional embodiments may be implemented, without departing from the broader scope of the disclosed embodiments as set forth in the claims that follow.

What is claimed is:

1. A system for intra-operative use during a surgical procedure, comprising:
   a tracing platform configured to rigidly attach to an anatomy of a patient and having at least one surface configured to provide a defined path for tracing by a surgical instrument; and
   an intra-operative computing unit configured to:
     obtain path definition data related to the defined path;
     receive first pose data at a first instance of time from a tracking system related to the surgical instrument tracing the defined path and first landmark pose data corresponding to a landmark of the anatomy;
     calculate a first location of the defined path using the first pose data, the first landmark pose data and the path definition data;
     receive second pose data at a second instance of time from a tracking system related to the surgical instrument tracing the defined path and second landmark pose data corresponding to the landmark of the anatomy;
     calculate a second location of the defined path using the second pose data, the second landmark pose data and the path definition data;
     receive additional pose data corresponding to a joint of the anatomy;
     calculate a parameter using a change in the first location of the defined path and the second location of the defined path, and additional pose data;
     provide the parameter for display to a display unit; and
     present workflow via a display to guide a user to generate the first pose data at the first instance of time and to generate the second pose data at the second instance of time in association with steps of the surgical procedure.

2. The system of claim 1, wherein the defined path is provided by a groove in the at least one surface, the groove having a pair of sides closed along a bottom thereof by a bottom surface of the tracing platform, to receive and constrain a tip of the surgical instrument so that the tip has a consistent position throughout a trace of the bottom of the groove.

3. The system of claim 1, wherein the defined path is provided by a groove in the at least one surface, wherein the groove comprises a V-groove having a pair of sides joined together at respective ends thereof to form a bottom.

4. A system, for intra-operative use during a surgical procedure, comprising:
   a tracing platform configured to rigidly attach to an anatomy of a patient and having at least one surface configured to provide a defined path for tracing by a surgical instrument; and
   an intra-operative computing unit configured to:
     obtain path definition data related to the defined path;
     receive first pose data at a first instance of time from a tracking system related to the surgical instrument tracing the defined path and first landmark pose data corresponding to a landmark of the anatomy;
     calculate a first location of the defined path using the first pose data, the first landmark pose data and the path definition data;
     receive second pose data at a second instance of time from a tracking system related to the surgical instrument tracing the defined path and second landmark pose data corresponding to the landmark of the anatomy;
     calculate a second location of the defined path using the second pose data, the second landmark pose data and the path definition data;
     receive additional pose data corresponding to a joint of the anatomy;
     calculate a parameter using a change in the first location of the defined path and the second location of the defined path, and additional pose data; and
     provide the parameter for display to a display unit;
   wherein the anatomy is a femur, the first instance of time is prior to a positioning of an implant, the second instance of time is after the positioning of the implant and the parameter is a change in leg length.

5. The system of claim 4, wherein the defined path is provided by a groove in the at least one surface, the groove having a pair of sides closed along a bottom thereof by a bottom surface of the tracing platform, to receive and constrain a tip of the surgical instrument so that the tip has a consistent position throughout a trace of the bottom of the groove.

6. The system of claim 4, wherein the defined path is provided by a groove in the at least one surface, wherein the groove comprises a V-groove having a pair of sides joined together at respective ends thereof to form a bottom.

7. A system, for intra-operative use during a surgical procedure, comprising:
   a tracing platform configured to rigidly attach to an anatomy of a patient and having at least one surface configured to provide a defined path for tracing by a surgical instrument; and
   an intra-operative computing unit configured to:
     obtain path definition data related to the defined path;
     receive first pose data at a first instance of time from a tracking system related to the surgical instrument tracing the defined path and first landmark pose data corresponding to a landmark of the anatomy;
     calculate a first location of the defined path using the first pose data, the first landmark pose data and the path definition data;
     receive second pose data at a second instance of time from a tracking system related to the surgical instrument tracing the defined path and second landmark pose data corresponding to the landmark of the anatomy;
     calculate a second location of the defined path using the second pose data, the second landmark pose data and the path definition data;

receive additional pose data corresponding to a joint of the anatomy;

calculate a parameter using a change in the first location of the defined path and the second location of the defined path, and additional pose data; and provide the parameter for display to a display unit;

wherein the anatomy is a femur, the first instance of time is prior to a positioning of an implant, the second instance of time is after the positioning of the implant and the parameter is a change in leg offset.

8. The system of claim 7, wherein the defined path is provided by a groove in the at least one surface, the groove having a pair of sides closed along a bottom thereof by a bottom surface of the tracing platform, to receive and constrain a tip of the surgical instrument so that the tip has a consistent position throughout a trace of the bottom of the groove.

9. The system of claim 7, wherein the defined path is provided by a groove in the at least one surface, wherein the groove comprises a V-groove having a pair of sides joined together at respective ends thereof to form a bottom.

10. A computer-implemented method for intra-operative use during a surgical procedure by an intra-operative computing unit comprising at least one processing unit, the method comprising the steps of:

obtaining, by the at least one processing unit, path definition data related to a trace of a defined path on at least one surface of a tracing platform, the tracing platform configured to rigidly attach to an anatomy of a patient;

receiving, by the at least one processing unit, first pose data at a first instance of time from a tracking system related to a surgical instrument tracing the defined path and first landmark pose data corresponding to a landmark of the anatomy;

calculating, by the at least one processing unit, a first location of the defined path using the first pose data, first landmark pose data corresponding to a landmark of the anatomy and the path definition data;

receiving, by the at least one processing unit, second pose data at a second instance of time from a tracking system related to the surgical instrument tracing the defined path and second landmark pose data corresponding to the landmark of the anatomy;

calculating, by the at least one processing unit, a second location of the defined path using the second pose data, the second landmark pose data and the path definition data;

receiving, by the at least one processing unit, additional pose data comprising pose data corresponding to a center of rotation of a joint of the anatomy;

calculating, by the at least one processing unit, a parameter using a change in the first location of the defined path and the second location of the defined path, and the additional pose data;

providing, by the at least one processing unit, the parameter for display to a display unit; and presenting workflow, by the at least one processing unit, via a display to guide a user to generate the first pose data at the first instance of time and to generate the second pose data at the second instance of time in association with steps of the surgical procedure.

11. The method of claim 10, wherein the defined path is provided by a groove in the at least one surface, the groove having a pair of sides closed along a bottom thereof by a bottom surface of the tracing platform, to receive and constrain a tip of the surgical instrument so that the tip has a consistent position throughout a trace of the bottom of the groove.

12. The method of claim 10, wherein the defined path is provided by a groove in the at least one surface, wherein the groove comprises a V-groove having a pair of sides joined together at respective ends thereof to form a bottom.

* * * * *